(12) United States Patent
Kurihara et al.

(10) Patent No.: US 8,568,791 B2
(45) Date of Patent: Oct. 29, 2013

(54) ANTIBACTERIAL ZEOLITE PARTICLES AND ANTIBACTERIAL RESIN COMPOSITION

(75) Inventors: Yasuo Kurihara, Nagoya (JP); Kumiko Miyake, Nagoya (JP); Masashi Uchida, Nagoya (JP)

(73) Assignee: Sinanen Zeomic Co., Ltd., Nagoya (JP)

( * ) Notice: Subject to any disclaimer, the term of this patent is extended or adjusted under 35 U.S.C. 154(b) by 1161 days.

(21) Appl. No.: 11/798,829

(22) Filed: May 17, 2007

(65) Prior Publication Data

US 2007/0298128 A1   Dec. 27, 2007

(30) Foreign Application Priority Data

Jun. 22, 2006   (JP) ................................ 2006-172327

(51) Int. Cl.
  *A01N 59/06*  (2006.01)
  *A01N 59/16*  (2006.01)
  *A01N 25/08*  (2006.01)
  *C01B 39/00*  (2006.01)

(52) U.S. Cl.
  USPC ........... 424/618; 424/409; 424/489; 424/641; 424/642; 424/684; 423/700

(58) Field of Classification Search
  USPC ................. 424/489, 618, 641, 409, 642, 684; 423/700
  See application file for complete search history.

(56) References Cited

U.S. PATENT DOCUMENTS 4,911,899 A * 3/1990 Hagiwara et al. ............. 423/700

FOREIGN PATENT DOCUMENTS

| CN | 1253729 | 5/2000 |
|---|---|---|
| CN | 1762218 | 4/2006 |
| EP | 0270129 | 6/1988 |
| JP | 63-265809 | 11/1988 |
| JP | 04-021517 | 1/1992 |
| JP | 04-224505 | 8/1992 |
| JP | 06-183728 | 7/1994 |
| KR | 2003-0013140 | 2/2003 |

OTHER PUBLICATIONS

HCAPLUS Abstract 2006:406224 (abstracting, CN 1762219, Apr. 26, 2006), abstract published May 4, 2006.*
Korean Office Action dated Aug. 29, 2008 issued in counterpart Korean Application No. 9-5-2008-045342473 with English translation.
European Search Report issued for European Patent Application No. 07110876.5-1219, dated Jan. 31, 2012.
Japanese Office Action issued for JP Patent Application No. 2006-172327, dated Jul. 25, 2011 with English translation.

* cited by examiner

*Primary Examiner* — John Pak
(74) *Attorney, Agent, or Firm* — Nixon & Vanderhye PC

(57) ABSTRACT

The present invention herein provides antibacterial zeolite particles whose ion-exchangeable ions have completely or partially been replaced with silver ions and zinc ions, wherein the ratio (A/B) of the silver ion concentration (A) to the zinc ion concentration (B) in the antibacterial zeolite particles increases in the direction along the depth of each zeolite particle. The antibacterial zeolite particles show excellent discoloration-resistant characteristics, while maintaining their excellent antibacterial activities. Accordingly, the antibacterial zeolite particles can suitably be applied to all sorts of products that are required to have antibacterial properties.

4 Claims, No Drawings

ANTIBACTERIAL ZEOLITE PARTICLES AND ANTIBACTERIAL RESIN COMPOSITION

This application claims the benefit of priority to JP 2006-172327 filed on Jun. 22, 2006, the entire contents of which is hereby incorporated by reference.

TECHNICAL FIELD

The present invention relates to antibacterial zeolite particles and an antibacterial resin composition containing the particles. More particularly, the present invention relates to antibacterial zeolite particles and an antibacterial resin composition containing the particles, which possess discoloration-resistant characteristics.

BACKGROUND ART

There have been well-known antibacterial zeolite particles which are prepared by replacing ion-exchangeable metal ions present in zeolite particles with antibacterial metal ions such as silver, copper and/or zinc ions and an antibacterial composition containing the same. In this respect, however, it has been known that an antibacterial resin composition obtained by incorporating such antibacterial zeolite particles into a resin undergoes a color change with the elapse of time. As a means for solving such a problem of color change with time, associated with the conventional antibacterial zeolite particles, there has already been developed a technique in which ammonium ions are incorporated into antibacterial zeolite particles (see Patent Document 1 specified later).

The antibacterial zeolite particles disclosed in this Patent Document 1 would certainly serve as an excellent antibacterial agent and, more specifically, the latter is excellent in the durability of its antibacterial action or power when it is left in air or in water and it never undergoes any quality-deterioration even when it is incorporated into a resin through kneading. The antibacterial zeolite particles are free of any extreme color change under the usual use conditions, but when it is exposed to severe conditions, for instance, it is irradiated with intensive ultraviolet light rays over a long period of time, the zeolite particles suffer from a problem in that it would undergo a color change with the elapse of time. Although the zeolite per se never loses its antibacterial action due to these color changes, a resin product to which the antibacterial zeolite particles are added may often undergo a color change. This in turn results in the considerable deterioration of the commercial value of the resin product depending on the kind thereof.

Patent Document 1: Japanese Unexamined Patent Publication Sho 63-265809

DISCLOSURE OF THE INVENTION

Accordingly, it is an object of the present invention to provide antibacterial zeolite particles which have discoloration-resistant characteristics and which can, in turn, be incorporated into a resin to give an antibacterial resin composition which is less likely to undergo a color change of the resin with the elapse of time.

It is another object of the present invention to provide an antibacterial resin composition which comprises the foregoing antibacterial zeolite particles.

The inventors of the present invention have conducted various studies to achieve the foregoing objects and as a result, have found that antibacterial zeolite particles possessing excellent discoloration-resistant characteristics can be obtained by controlling the ratio of the silver ion concentration (A) to the zinc ion concentration (B) in antibacterial zeolite particles whose ion-exchangeable ions have completely or partially been replaced with silver ions and zinc ions, in such a manner that the ratio (A/B) increases in the direction along the depth of each zeolite particle. The present invention has been completed on the basis of such a finding.

The present invention thus herein provides the following antibacterial zeolite particles and an antibacterial resin composition containing the same:

(1) Antibacterial zeolite particles whose ion-exchangeable ions have completely or partially been replaced with silver ions and zinc ions, wherein the ratio (A/B) of the silver ion concentration (A) to the zinc ion concentration (B) in the antibacterial zeolite particles increases in the direction along the depth of each zeolite particle;

(2) Antibacterial zeolite particles whose ion-exchangeable ions have completely or partially been replaced with silver ions and zinc ions, wherein they have a ratio: (X/Y) of less than 1, in which (X) represents the ratio of the silver ion concentration to the zinc ion concentration as determined for the region within the zeolite particles extending over the depth ranging from 0 to 1 nm from the surface of the zeolite particles and (Y) represents the ratio of the silver ion concentration to the zinc ion concentration as determined for the region within the zeolite particles extending over the depth ranging from 5 to 10 nm from the surface of the zeolite particles;

(3) The antibacterial zeolite particles as set forth in the foregoing item (2), wherein the ratio: (X/Y) ranges from 0.6 to 0.4, in which (X) represents the ratio of the silver ion concentration to the zinc ion concentration as determined for the region within the zeolite particles extending over the depth ranging from 0 to 1 nm from the surface of the zeolite particles and (Y) represents the ratio of the silver ion concentration to the zinc ion concentration as determined for the region within the zeolite particles extending over the depth ranging from 5 to 10 nm from the surface of the zeolite particles;

(4) An antibacterial resin composition comprising antibacterial zeolite particles as set forth in any one of the foregoing items (1) to (3) and a resin; and (5) The antibacterial resin composition as set forth in the foregoing item (4), wherein the composition comprises the antibacterial zeolite particles in an amount ranging from 0.05 to 80% by mass on the basis of the total mass of the resin composition.

The antibacterial zeolite particles according to the present invention show excellent discoloration-resistant characteristics as will be demonstrated in Examples described later. Accordingly, the present invention can suitably be applied to all sorts of products that are required to have antibacterial properties (antibacterial products).

BEST MODE FOR CARRYING OUT THE INVENTION

The present invention will hereunder be described in more detail.

The present invention relates to antibacterial zeolite particles whose ion-exchangeable ions have completely or partially been replaced with silver ions and zinc ions, wherein the ratio (A/B) of the silver ion concentration (A) to the zinc ion concentration (B) in the antibacterial zeolite particles increases in the direction along the depth of each zeolite particle.

The "zeolite" which constitutes the antibacterial particles of the present invention may be either naturally occurring one or synthetic one.

The zeolite is in general an alumonosilicate having a three-dimensional skeletal structure and is represented by the following general formula: $xM_{2/n}O.Al_2O_3.ySiO_2.zH_2O$. In this general formula, M represents an ion-exchangeable n-valent ion and it is usually a mono-valent or di-valent metal ion; x represents the molar number of the metal oxide; y represents the molar number of the silica; and z represents the molar number of the crystal water.

Specific examples of zeolite materials are zeolite A, zeolite X, zeolite Y, zeolite T, zeolite having a high silica content, sodalite, mordenite, analcime, clinoptilolite, chabazite, and erionite, but the present invention is not restricted to these specific zeolite materials at all.

The particle size of the antibacterial zeolite particles according to the present invention is not restricted to any particular range, but the zeolite particles have an average particle size ranging from 0.1 to 20 μm, preferably 0.4 to 9.0 μm and particularly preferably 0.7 to 3.5 μm, from the viewpoint of the enhanced antibacterial effect thereof due to their increased surface area and the easiness of their incorporation into resins. In this connection, the particle size of the zeolite particles can be determined according to the particle size distribution-determining technique, which makes use of a laser.

The ion-exchange capacities of these exemplified zeolite materials are typically 7 meq/g for the zeolite A, 6.4 meq/g for the zeolite X, 5 meq/g for the zeolite Y, 3.4 meq/g for the zeolite T, 11.5 meq/g for the sodalite, 2.6 meq/g for the mordenite, 5 meq/g for the analcime, 2.6 meq/g for the clinoptilolite, 5 meq/g for the chabazite, and 3.8 meq/g for the erionite. All of these zeolite materials possess ion-exchange capacities which are high enough to undergo ion-exchange with silver and zinc ions.

Examples of ion-exchangeable ions present in zeolite materials are sodium ions, calcium ions, potassium ions, magnesium ions, and/or iron ions.

In the present invention, the whole or a part of the ion-exchangeable ions present in zeolite materials are completely or partially replaced (ion-exchanged) with silver and zinc ions serving as antibacterial metal ions to thus impart antibacterial properties to the zeolite materials.

It would be sufficient that the silver ions concentration in the antibacterial zeolite particles is more than or equal to 0.02% by mass, but it preferably ranges from 0.1 to 15% by mass while taking into consideration the antibacterial properties of the zeolite particles. In this specification, the unit "%" used for expressing the ion concentration present in the zeolite particles means "% by mass" as expressed on the basis of the mass of the zeolite dried at a temperature of 110° C.

Similarly, it would be sufficient that the zinc ion concentration in the antibacterial zeolite particles is more than or equal to 0.05% by mass and preferably 0.1 to 8% by mass while taking into consideration the antibacterial properties of the zeolite particles.

In the antibacterial zeolite particles of the present invention, the ratio (A/B) of the silver ion concentration (A) to the zinc ion concentration (B) in the particles (hereunder also referred to as "silver/zinc ion concentration ratio") increases in the direction along the depth of each zeolite particle. Accordingly, the antibacterial zeolite particles can acquire more excellent discoloration-resistant characteristics. In this respect, the term "the direction along the depth of the particles" herein used means the direction from the surface of the particle toward the interior thereof.

The increase of the silver/zinc ion concentration ratio can be evaluated by establishing two regions within the antibacterial zeolite particles, which differ, from one another, in the depth from the surface of the particles, determining the silver/zinc ion concentration ratios in these two regions and comparing them with one another. For instance, the increase in the silver/zinc ion concentration ratio can be evaluated as follows: these two regions are defined to be one extending over the depth ranging from 0 to 1 nm from the surface of the zeolite particle and one extending over the depth ranging from 5 and 10 nm from the surface of the zeolite particle, the silver and zinc ion concentrations in these two regions are determined, the silver/zinc ion concentration ratios in these two regions are calculated and then the resulting concentration ratios are compared to one another.

In this case, the ratio: (X/Y) should be less than 1, in which (X) represents the ratio of the silver ion concentration to the zinc ion concentration as determined for the region within the zeolite particles extending over the depth ranging from 0 to 1 nm from the surface of the particles and (Y) represents the ratio of the silver ion concentration to the zinc ion concentration as determined for the region within the zeolite particles extending over the depth ranging from 5 to 10 nm from the surface of the particles. The ratio (X/Y) preferably ranges from 0.6 to 0.2 and particularly preferably 0.6 to 0.4.

The antibacterial zeolite particles may acquire particularly excellent discoloration-resistant properties when adjusting the ratio: (X/Y) in such a manner that it falls within the range of from 0.6 to 0.3, wherein (X) represents the ratio of the silver ion concentration to the zinc ion concentration in the region extending over the depth ranging from 0 to 1 nm from the particle surface and (Y) represents the ratio of the silver ion concentration to the zinc ion concentration in the region extending over the depth ranging from 5 to 10 nm from the particle surface.

The ion concentrations in specific regions positioned within each antibacterial zeolite particle (the region extending over the depth ranging from 0 to 1 nm from the zeolite particle surface and the region extending over the depth ranging from 5 to 10 nm from the zeolite particle surface) can be determined by treating the antibacterial zeolite particles with an acid to thus dissolve each corresponding region and then determining the concentration of each ion present in the resulting liquid phase. This method makes use of such a phenomenon that the ions incorporated into the zeolite particles through the ion-exchange operation are dissolved into the liquid phase because of such properties of the zeolite that the aluminum component constituting the same is relatively susceptible to the attack of acids.

The procedures for the determination of these ion concentrations will be described below in detail, by way of example.

The silver and zinc ion concentrations in the region within each antibacterial zeolite particle, extending over the depth ranging from 0 to 1 nm from the surface of the zeolite particle can be determined according to the method comprising the following procedures:

(1) To 50 mL of a 0.0001N aqueous solution of nitric acid, there is added 5 g of powdery antibacterial zeolite (having an average particle size of 2.5 μm), followed by the stirring of the resulting mixture at 20° C. for one hour to thus dissolve the region extending over the depth ranging from 0 to 1 nm from the zeolite particle surface out from the particles;

(2) The resulting solid-liquid mixture is filtered through a membrane filter (pore diameter: 0.05 μm) and further the membrane filter is washed with water to thus give a liquid phase (filtrate+wash liquid);

(3) The resulting liquid phase is quantitatively inspected for the silver and zinc ion concentrations, respectively.

In addition, the silver and zinc ion concentrations in the region within each antibacterial zeolite particle, extending over the depth ranging from 5 to 10 nm from the surface of the zeolite particle can be determined by the method comprising the following procedures:

(1) To 50 mL of a 0.0003N aqueous solution of nitric acid, there is added 5 g of powdery antibacterial zeolite (having an average particle size of 2.5 µm), followed by the stirring of the resulting mixture at 20° C. for 4 hour to thus dissolve the region extending over the depth ranging from 0 to 5 nm from the zeolite particle surface out from the particles;

(2) The resulting solid-liquid mixture is filtered through a membrane filter (pore diameter: 0.05 µm) and further the membrane filter is washed with water to thus give the antibacterial zeolite particles whose region extending over the depth ranging from 0 to 5 nm from the zeolite particle surface is dissolved away;

(3) The zeolite particles obtained in the foregoing step (2) are introduced into 50 mL of a 0.001N aqueous solution of nitric acid and then the resulting mixture is stirred at 20° C. for 1.5 hour;

(4) The resulting solid-liquid mixture is filtered through a membrane filter (pore diameter: 0.05 µm) and the membrane filter is further washed with water to thus give a liquid phase (filtrate+wash liquid);

(5) The resulting liquid phase is quantitatively inspected for the silver and zinc ion concentrations, respectively.

The procedures described above may be applied not only to the foregoing zeolite particles having an average particle size of 2.5 µm, but also to other particles having different particle sizes (for instance, those having an average particle size ranging from 0.1 to 20 µm).

In this connection, the silver ion concentration in the liquid phase can be determined according to, for instance, the atomic-absorption spectroscopy. The zinc ion concentration in the liquid phase can likewise be determined according to, for instance, the atomic-absorption spectroscopy.

The foregoing method would permit the precise determination of desired ion concentrations in the regions extending over the depth ranging from 0 to 1 nm from the zeolite particle surface and extending over the depth ranging from 5 to 10 nm from the surface of the zeolite particle, respectively. This will be demonstrated in the Reference Examples given below.

The antibacterial zeolite particles whose silver/zinc ion concentration ratio increases along the direction of the depth of the particles can be prepared by using any one of the following three methods, upon the replacement of ion-exchangeable ions present in the zeolite particles with the desired ions. However, the method for producing the antibacterial zeolite particles is not restricted to these specific ones at all.

1. A method which comprises the step of replacing ion-exchangeable ions with silver and zinc ions while using a reaction solution whose ratio of the silver ion concentration to the zinc ion concentration is gradually changed with time;

2. A method for replacing ion-exchangeable ions with silver and zinc ions, which comprises the steps of first carrying out the ion-exchange treatment in the presence of only silver ions and then carrying out the ion-exchange treatment in the coexistence of silver and zinc ions; and 3. A method for replacing ion-exchangeable ions with silver and zinc ions, in which the ion-exchange treatment is carried out according to the following two stages: the first ion-exchange stage carried out using a silver ion-containing reaction solution; and the second ion-exchange stage carried out using a zinc ion-containing reaction solution.

In the first method, the replacement of ion-exchangeable ions, present in the zeolite particles, with silver and zinc ions is carried out using a reaction solution in which the ratio of the silver ion concentration to the zinc ion concentration is gradually changed with time.

For instance, as will be described in Example 1 given later, the first method can be practiced by initiating the ion-exchange reaction using a reaction solution having desired silver and zinc ion concentrations and subsequently, continuing the ion-exchange reaction while increasing, with time, only the zinc ion concentration of the reaction solution.

The zeolite particles may be brought into contact with the reaction solution, in a continuous or batch-wise process, at a temperature ranging from 10 to 70° C., preferably 30 to 60° C. over a time ranging from 3 to 24 hours, preferably 10 to 24 hours.

It is suitable in the present invention to adjust the pH value of the reaction solution at a level ranging from 3 to 10 and preferably 5 to 8. The pH adjustment of the reaction solution is preferable since any deposition of, for instance, silver oxide on the surface of the zeolite particles and/or within fine pores present therein can be prevented.

Each ion may in general be supplied to the reaction solution in the form of a salt thereof. The silver ions can be supplied to the reaction solution using, for instance, silver nitrate, silver sulfate, silver perchlorate, silver acetate, diammine silver nitrate and diammine silver sulfate. The zinc ions can be supplied to the reaction solution using, for instance, zinc nitrate, zinc sulfate, zinc perchlorate, zinc acetate and zinc thioironate.

In the second method, the ion-exchange treatment is first carried out in the presence of only silver ions and the ion-exchange treatment is then carried out in the coexistence of both silver and zinc ions. In this respect, the conditions (time and temperature) for these two ion-exchange reactions may be the same or different from one another.

The first ion-exchange in the presence of silver ions can be carried out at a temperature ranging from 10 to 95° C., preferably 50 to 85° C. for a time ranging from 3 to 24 hours, preferably 8 to 16 hours.

The second ion-exchange in the coexistence of both silver and zinc ions can be carried out at a temperature ranging from 10 to 95° C., preferably 35 to 65° C. for a time ranging from 3 to 24 hours, preferably 3 to 10 hours.

As will be described in Example 2 given later, the second method can be carried out by (1) initially mixing a slurry containing zeolite particles with a silver ion-containing solution (provided that the solution is free of any zinc ion) to cause a reaction between them at 80° C. for 10 hours and to thus replace ion-exchangeable ions in the zeolite with silver ions; and then (2) adding a zinc ion-containing solution to the resulting slurry to cause a reaction between them in the coexistence of both silver and zinc ions at 50° C. for 6 hours and to thus replace ion-exchangeable ions in the zeolite with silver and zinc ions.

In this connection, each ion can be supplied to the reaction solution using a salt of the corresponding ion such as those described above in connection with the first method.

In the third method, the ion-exchangeable ions present in the zeolite particles can be replaced with silver and zinc ions according to the following two stages: the first ion-exchange stage carried out using a silver ion-containing reaction solution; and the second ion-exchange stage carried out using a zinc ion-containing reaction solution.

For instance, as will be described in Example 3 given later, the third method can be carried out by separately preparing a first reaction solution containing silver ions and a second reaction solution containing zinc ions, first replacing ion-exchangeable ions in the zeolite particles with silver ions using the first reaction solution and then replacing ion-exchangeable ions in the zeolite particles with zinc ions using the second reaction solution.

The zeolite particles are brought into contact with each reaction solution at a temperature ranging from 10 to 70° C., preferably 30 to 60° C. for a time ranging from 3 to 24 hours, preferably 10 to 24 hours, according to a continuous or batch-wise process.

The pH value of each reaction solution is suitably set at a level ranging from 3 to 10 and preferably 5 to 7. The pH adjustment of the reaction solution is preferable since any deposition of, for instance, silver oxide on the surface of the zeolite particles and/or within fine pores present therein can be prevented.

In this connection, each ion can be supplied to the reaction solution using a salt containing the corresponding ion such as those described above in connection with the first method.

The zeolite particles obtained after the ion-exchange treatment are sufficiently washed with water and then dried. The zeolite particles are preferably dried under ordinary pressure and at a temperature ranging from 105 to 115° C., or under a reduced pressure ranging from 133 Pa (1 Torr) to 4000 Pa (30 Torr) and at a temperature ranging from 70 to 90° C.

To enhance the antibacterial action of the antibacterial zeolite particles, other antibacterial metal ions can be introduced into the zeolite particles in addition to the foregoing silver and zinc ions and specific examples thereof are copper ions, mercury ions, lead ions, tin ions, bismuth ions, cadmium ions, chromium ions and thallium ions.

These ions may in general be incorporated into the reaction solution in the form of salts thereof. Copper ions may be introduced into the reaction solution using, for instance, copper nitrate, copper sulfate, copper perchlorate, copper acetate and potassium tetracyano-cuprate. Mercury ions may be incorporated into the reaction solution using, for instance, mercury nitrate, mercury perchlorate and mercury acetate. Lead ions may be incorporated into the reaction solution using, for instance, lead sulfate and lead nitrate. Tin ions may be incorporated into the reaction solution using, for instance, tin sulfate. Bismuth ions may be incorporated into the reaction solution using, for instance, bismuth chloride and bismuth iodide. Cadmium ions may be incorporated into the reaction solution using, for instance, cadmium perchlorate, cadmium sulfate, cadmium nitrate and cadmium acetate. Chromium ions may be incorporated into the reaction solution using, for instance, chromium perchlorate, chromium sulfate, chromium ammonium sulfate and chromium nitrate. Further, thallium ions may be incorporated into the reaction solution using, for instance, thallium perchlorate, thallium sulfate, thallium nitrate and thallium acetate.

In this respect, when carrying out the ion-exchange treatment using ions such as tin and bismuth ions, which have only a small number of suitable water-soluble salts, the ion-exchange treatment may be carried out using a solution in an organic solvent such as an alcohol or acetone and thus the ion-exchange treatment can be completed without being accompanied by any deposition of a hardly soluble-basic salt.

To further improve the discoloration-resistant characteristics of the zeolite particles, it is also possible to incorporate ammonium ions, amine ions and hydrogen ions or the like into the zeolite particles, in addition to the silver and zinc ions.

These ions may in general be incorporated into the reaction solution in the form of salts thereof. Ammonium ions may be incorporated into the reaction solution using, for instance, ammonium nitrate, ammonium sulfate, ammonium acetate, ammonium perchlorate, ammonium thiosulfate and ammonium phosphate. Hydrogen ions may be incorporated into the reaction solution using, for instance, nitric acid, sulfuric acid, acetic acid, perchloric acid and phosphoric acid. Moreover, hydrogen ions may likewise be incorporated into the reaction solution through the heat decomposition of ammonium ions.

The concentration of ammonium ions in the zeolite particles desirably ranges from 0.10 to 2.0% by mass and that of hydrogen ions therein desirably ranges from 0.10 to 2.0% by mass from the viewpoint of the improvement of the discoloration-resistant characteristics of the resulting antibacterial zeolite particles.

The antibacterial zeolite particles of the present invention thus obtained possess antibacterial activity against a variety of common bacteria, fungi and yeast (including the prevention and control of the generation and proliferation of these bacterial cells as well as the extinction thereof). In this respect, the term "antibacterial properties (effects)" used herein also includes the effects of preventing and controlling the generation and proliferation of fungi and/or algae as well as the effect of killing the same (mold-proofing and antialgal effects).

The antibacterial activity of the zeolite particles can be evaluated by the determination of the minimum growth-inhibitory concentration (MIC) thereof against a variety of common bacteria, fungi and yeast. The MIC value can be defined to be a value determined by, for instance, smearing a solution for the inoculation of a bacterium onto the surface of a plate culture medium containing each candidate antibacterial zeolite in an arbitrary concentration and then incubating the inoculated medium to thus determine the minimum concentration of the antibacterial zeolite required for the inhibition of any growth of these microorganisms.

The antibacterial zeolite particles of the present invention can be incorporated into a resin to thus give an antibacterial resin composition. In this respect, examples of such resins usable herein include thermoplastic and heat-curable resins such as polyethylenes, polypropylenes, vinyl chloride resins, ABS resins, polyesters, polyvinylidene chlorides, polyamides, polystyrenes, polyacetals, polyvinyl alcohols, polycarbonates, acrylic resins, polyurethanes, phenolic resins, urea resins, melamine resins, epoxy resins, fluoro-plastics, rayons, cuprammonium rayons, acetate resins, various kinds of elastomers, and naturally occurring and synthetic rubber materials.

The antibacterial resin composition of the present invention can be, for instance, prepared by directly incorporating the foregoing antibacterial zeolite particles into one of the foregoing resins or by coating the surface of a resin with the antibacterial zeolite particles. The content of the antibacterial zeolite particles in the antibacterial resin composition desirably ranges from 0.05 to 80% by mass and preferably 0.1 to 80% by mass on the basis of the total mass of the antibacterial resin composition from the viewpoint of the impartment, to the resin, of antibacterial, antifungal and/or antialgal functions. In this connection, the MIC values of the antibacterial resin composition can be evaluated according to the same method described above.

In addition, the content of the antibacterial zeolite in the antibacterial resin composition preferably ranges from 0.1 to 3% by mass from the viewpoint of the prevention of any color change of the resin.

The foregoing antibacterial zeolite particles of the present invention can be incorporated into fibrous materials other than the foregoing resins. Examples of such fibrous materials are paper.

Furthermore, the foregoing antibacterial zeolite particles and antibacterial resin composition of the present invention can be used in a variety of fields. In particular, the antibacterial resin composition of the present invention would quite hardly cause discoloration with time and accordingly, it can suitably be used in products having a pale color (white to pastel) of the initial outside appearance.

For instance, in the field of aqueous systems, they can be used as antibacterial and/or antialgal agents used in, for instance, water purifiers or those for the water of cooling towers and a variety of cooling water, and they can also be used as elixirs of life for cut flowers.

In the field of the paints and varnishes, they can be used for imparting the antibacterial, antifungal and/or antialgal functions to the surface of a coated layer by, for instance, directly incorporating them into a variety of paints and varnishes such as oil-based ones, lacquers, varnishes, alkyd resin type ones, amino alkyd resin type ones, vinyl resin type ones, acrylic resin type ones, epoxy resin type ones, urethane resin type ones, aqueous emulsified resin type ones, powder coatings, chlorinated rubber coatings, and phenolic resin type ones, or by applying the zeolite particles or the resin composition onto the surface of a coated layer.

In the field of the construction, it would be possible to impart the antibacterial, antifungal and/or antialgal functions to the surface of architectural materials such as jointing materials, wall materials and tiles by incorporating them into these architectural materials or by applying the same onto the surface of these architectural materials.

In the field of the paper-making or paper industry, it would be possible to impart the antibacterial and/or antifungal functions to various paper materials such as wet tissues, paper packing materials, corrugated boards, sheets of paper for spreading and freshness-keeping paper by the incorporation of the zeolite particles or the resin composition into these paper materials during the process for the manufacture of the paper materials, or by applying the same onto the surface of these paper materials. Alternatively, it is also possible to use the zeolite particles or the resin composition, in particular, as a slime-controlling agent.

The antibacterial zeolite particles and antibacterial resin composition of the present invention can be applied to all of the fields which require the inhibition and/or prevention of the generation and growth or proliferation of various microorganisms such as a variety of common bacteria, fungi, yeast and algae, and/or the extinction thereof, in addition to the aforementioned fields.

The present invention will hereunder be described in more detail with reference to the following Examples, but the present invention is not restricted to these specific Examples at all.

EXAMPLES

Reference Example

Before the description of Examples, it was first confirmed whether, or not, the treatment of antibacterial zeolite particles with an acid permits the determination of ion concentrations in specific regions extending over specific ranges of the depth of the zeolite particles (the region extending over the depth ranging from 0 to 1 nm from the particle surface and that extending over the depth ranging from 5 to 10 nm from the particle surface).

As a sample for the determination, there were used zeolite particles obtained by completely replacing all of the ion-exchangeable ions present in Zeolite A particles with silver ions (in other words, silver ions are uniformly distributed within the particles) (silver ion concentration: 47.5% by mass; density: 2.1 g/cm$^3$; shape: a cubic one; average particle size (the length of each side): 1.5 µm) (This sample is hereunder referred to as "silver-zeolite particle(s)").

This verification was carried out by comparing the silver ion content determined through the acid treatment (measured or found value) to that (theoretical value) calculated on the basis of the chemical theory.

1. Determination of Ag Ion Content in Silver-Zeolite Particles by the Acid-Treatment:

(1) Ag Ion Content in Region Extending over Depth Ranging from 0 to 1 nm from Particle Surface:

To 50 mL of a 0.0001N aqueous solution of nitric acid, there was added 5 g of silver-zeolite particles (in a powdery form), followed by the stirring of the resulting mixture at 20° C. for one hour (stirring rate: 150 rpm). The resulting solid-liquid mixture was filtered through a membrane filter (pore diameter: 0.05 µm) and further the membrane filter washed with water to thus give a liquid phase (filtrate+wash liquid). The resulting liquid phase was quantitatively inspected for the silver ion concentration according to the atomic-absorption spectroscopy. As a result, the silver ion content (measured value) was found to be 9.34 mg.

(2) Ag Ion Content in Region Extending over Depth Ranging from 5 to 10 nm from Particle Surface:

To 50 mL of a 0.0003N aqueous solution of nitric acid, there was added 5 g of silver-zeolite particles (in a powdery form), followed by the stirring of the resulting mixture at 20° C. for 4 hour (stirring rate: 150 rpm). The resulting solid-liquid mixture was filtered through a membrane filter (pore diameter: 0.05 µm) and further the membrane filter washed with water. The whole particles remaining on the membrane filter were introduced into 50 mL of a 0.001N aqueous solution of nitric acid and then the resulting mixture was stirred at 20° C. for 1.5 hour (stirring rate: 150 rpm). The resulting solid-liquid mixture was filtered through a membrane filter (pore diameter: 0.05 µm) and the membrane filter was further washed with water to thus give a liquid phase (filtrate+wash liquid). The resulting liquid phase was quantitatively inspected for the silver ion concentration according to the atomic-absorption spectroscopy. As a result, the silver ion content (measured value) was found to be 46.7 mg.

2. Calculation of Ag Ion Content in Silver-Zeolite Particles Based on Chemical Theory:

Silver ions are uniformly distributed within the silver-zeolite particles. Accordingly, the amount of silver ions present in a region extending over a range of depth from the particle surface can be calculated on the basis of the rate of the "volume of the region extending over a range of depth from the particle surface" with respect to the "total volume" of the particle.

The rate of the volume of the region extending over the depth ranging from 0 to 1 nm from the particle surface relative to the total volume of the silver-zeolite particle is 0.4% and the amount of silver ions present in this region is calculated to be 9.5 mg.

The rate of the region extending over the depth ranging from 5 to 10 nm from the particle surface relative to the total volume of the silver-zeolite particle is 2.0% and the amount of silver ions present in this region is calculated to be 47.5 mg.

The following Table shows the results obtained by comparing the amount of silver ions (measured value) determined according to the acid treatment with that (theoretical value) calculated on the basis of the chemical theory.

|  | Measured Value (mg) | Theoretical Value (mg) |
| --- | --- | --- |
| Amt. of Ag Ions Present in Region Extending Over Depth Ranging from 0 to 1 nm | 9.34 | 9.5 |
| Amt. of Ag Ions Present in Region Extending Over Depth Ranging from 5 to 10 nm | 46.7 | 47.5 |

The results listed in the foregoing Table clearly indicate that the amount of silver ions determined according to the acid treatment is almost consistent with that calculated on the basis of the chemical theory. Accordingly, it could be concluded as follows, on the basis of this result: Each particular ion concentration in a specific region of an antibacterial zeolite particle, extending over a specific range of depth (the region extending over the depth ranging from 0 to 1 nm from the particle surface and the region extending over the depth ranging from 5 to 10 nm from the particle surface) can be determined according to the foregoing acid-treating method.

In the following Examples and Comparative Examples, the following materials were used:

Zeolite materials used were Zeolite A ($Na_2O \cdot Al_2O_3 \cdot 1.9SiO_2 \cdot xH_2O$, having an average particle size of 1.5 μm and an ion-exchange capacity of 7 meq/g); Zeolite k ($Na_2O \cdot Al_2O_3 \cdot 2.3SiO_2 \cdot xH_2O$, having an average particle size of 2.5 μm and an ion-exchange capacity of 6.4 meq/g); and Zeolite Y ($Na_2O \cdot Al_2O_3 \cdot 4SiO_2 \cdot xH_2O$, having an average particle size of 0.7 μm and an ion-exchange capacity of 5 meq/g).

Silver nitrate ($AgNO_3$) was used for supplying silver ions to a reaction solution.

Zinc nitrate ($Zn(NO_3)_2$) was used for supplying zinc ions to a reaction solution.

In addition, to enhance the discoloration-resistant properties of the antibacterial zeolite particles, ammonium ions were used. Ammonium nitrate ($NH_4NO_3$) was used for supplying ammonium ions to a reaction solution.

In the following Examples and Comparative Examples, the silver and zinc ion concentrations in the region within each antibacterial zeolite particle, extending over the depth ranging from 0 to 1 nm from the surface of the zeolite particle were determined according to the method comprising the following procedures:

(1) To 50 mL of a 0.0001N aqueous solution of nitric acid, there was added 5 g of antibacterial zeolite particles (in a powdery form), followed by the stirring of the resulting mixture at 20° C. for one hour to thus dissolve the region extending over the depth ranging from 0 to 1 nm from the zeolite particle surface out from the particles;

(2) The resulting solid-liquid mixture was filtered through a membrane filter (pore diameter: 0.05 μm) and further the membrane filter washed with water to thus give a liquid phase (filtrate+wash liquid); and (3) The resulting liquid phase was quantitatively inspected for the silver and zinc ion concentrations, respectively.

The silver and zinc ion concentrations in the resulting liquid sample were quantitatively determined according to the atomic-absorption spectroscopy.

In the following Examples and Comparative Examples, the silver and zinc ion concentrations in the region within each antibacterial zeolite particle, extending over the depth ranging from 5 to 10 nm from the surface of the zeolite particle were determined by the method comprising the following procedures:

(1) To 50 mL of a 0.0003N aqueous solution of nitric acid, there was added 5 g of antibacterial zeolite particles (in a powdery form), followed by the stirring of the resulting mixture at 20° C. for 4 hour to thus dissolve the region extending over the depth ranging from 0 to 5 nm from the zeolite particle surface out from the particles;

(2) The resulting solid-liquid mixture was filtered through a membrane filter (pore diameter: 0.05 μm) and further the membrane filter washed with water to thus give the antibacterial zeolite particles whose region extending over the depth ranging from 0 to 5 nm from the zeolite particle surface was dissolved away;

(3) The zeolite particles obtained in the foregoing step (2) were introduced into 50 mL of a 0.001N aqueous solution of nitric acid and then the resulting mixture was stirred at 20° C. for 1.5 hour;

(4) The resulting solid-liquid mixture was filtered through a membrane filter (pore diameter: 0.05 μm) and the membrane filter was further washed with water to thus give a liquid phase (filtrate+wash liquid); and (5) The resulting liquid phase was quantitatively inspected for the silver and zinc ion concentrations, respectively.

The silver and zinc ion concentrations in the resulting liquid sample were quantitatively determined according to the atomic-absorption spectroscopy.

Example 1

In this Example 1, 5 kinds of antibacterial zeolite particle samples (Sample Nos. 1 to 5) were prepared using a reaction solution in which the silver and zinc ion concentrations were changed with time.

Preparation of Sample No. 1:

(1) To 1 kg of Zeolite A particles dried by heating at 110° C., there was added water to give 1.3 L of a slurry, the slurry was subsequently stirred to degas the same, a proper amount of a 0.5N nitric acid solution and water were further added to the slurry to thus give 1.8 L of a slurry whose pH value was adjusted to a level ranging from 5 to 7.

(2) To the slurry prepared in the foregoing stage (1), there was added 1.5 L of a solution (30° C.) containing 1.5 mole/L of ammonium nitrate and 0.01 mole/L of silver nitrate to give a slurry liquid and the latter was then stirred for 16 hours.

(3) To the slurry liquid prepared in the foregoing stage (2), there was added 1.5 L of a 0.15 mole/L zinc nitrate solution (30° C.) to give a slurry liquid (a reaction solution) having an overall volume of 4.8 L. The pH value of the reaction solution was found to be 7.3.

(4) The reaction solution prepared in the stage (3) was stirred at 30° C. and a stirring rate of 150 rpm over 16 hours to thus subject the zeolite particles to an ion-exchange reaction under ion-exchangeable equilibrium conditions. During the ion-exchange reaction, zinc nitrate was dissolved in the reaction solution to thus increase the zinc nitrate concentration of the reaction solution.

(5) The zeolite phase was separated from the reaction solution obtained in the foregoing stage (4) through filtration and then excess silver ions and zinc ions were removed by washing the filtered zeolite phase with water maintained at a temperature ranging from 15 to 60° C.

(6) The zeolite phase obtained in the foregoing stage (5) was dried by heating the same at 110° C. to thus form antibacterial zeolite particles which were hereunder referred to as Sample No. 1.

Preparation of Sample No. 2:

(1) To 1 kg of Zeolite A particles dried by heating at 110° C., there was added water to give 1.3 L of a slurry, the slurry was subsequently stirred to degas the same, a proper amount of a 0.5N nitric acid solution and water were further added to the slurry to thus give 1.8 L of a slurry whose pH value was adjusted to a level ranging from 5 to 7.

(2) To the slurry prepared in the foregoing stage (1), there was added 1.5 L of a solution (30° C.) containing 1.0 mole/L of ammonium nitrate and 0.08 mole/L of silver nitrate to give a slurry liquid and the latter was then stirred for 16 hours.

(3) To the slurry liquid prepared in the foregoing stage (2), there was added 1.5 L of a 0.10 mole/L zinc nitrate solution (30° C.) to give a slurry liquid (a reaction solution) having an overall volume of 4.8 L. The pH value of the reaction solution was found to be 7.1.

(4) The reaction solution prepared in the stage (3) was stirred at 30° C. and a stirring rate of 150 rpm over 16 hours to thus subject the zeolite particles to an ion-exchange reaction under ion-exchangeable equilibrium conditions. During the ion-exchange reaction, zinc nitrate was dissolved in the reaction solution to thus increase the zinc nitrate concentration of the reaction solution.

(5) The zeolite phase was separated from the reaction solution obtained in the foregoing stage (4) through filtration and then excess silver ions and zinc ions were removed by washing the filtered zeolite phase with water maintained at a temperature ranging from 15 to 60° C.

(6) The zeolite phase obtained in the foregoing stage (5) was dried by heating the same at 110° C. to thus form antibacterial zeolite particles which were hereunder referred to as Sample No. 2.

Preparation of Sample No. 3:

(1) To 1 kg of Zeolite A particles dried by heating at 110° C., there was added water to give 1.3 L of a slurry, the slurry was subsequently stirred to degas the same, a proper amount of a 0.5N nitric acid solution and water were further added to the slurry to thus give 1.8 L of a slurry whose pH value was adjusted to a level ranging from 5 to 7.

(2) To the slurry prepared in the foregoing stage (1), there was added 1.5 L of a solution (30° C.) containing 0.15 mole/L of silver nitrate to give a slurry liquid and the latter was then stirred for 16 hours.

(3) To the slurry liquid prepared in the foregoing stage (2), there was added 1.5 L of a 0.15 mole/L zinc nitrate solution (30° C.) to give a slurry liquid (a reaction solution) having an overall volume of 4.8 L. The pH value of the reaction solution was found to be 7.3.

(4) The reaction solution prepared in the stage (3) was stirred at 30° C. and a stirring rate of 150 rpm over 16 hours to thus subject the zeolite particles to an ion-exchange reaction under ion-exchangeable equilibrium conditions. During the ion-exchange reaction, zinc nitrate was dissolved in the reaction solution to thus increase the zinc nitrate concentration of the reaction solution.

(5) The zeolite phase was separated from the reaction solution obtained in the foregoing stage (4) through filtration and then excess silver ions and zinc ions were removed by washing the filtered zeolite phase with water maintained at a temperature ranging from 15 to 60° C.

(6) The zeolite phase obtained in the foregoing stage (5) was dried by heating the same at 110° C. to thus form antibacterial zeolite particles which were hereunder referred to as Sample No. 3.

Preparation of Sample No. 4:

(1) To 1 kg of Zeolite X particles dried by heating at 110° C., there was added water to give 1.3 L of a slurry, the slurry was subsequently stirred to degas the same, a proper amount of a 0.5N nitric acid solution and water were further added to the slurry to thus give 1.8 L of a slurry whose pH value was adjusted to a level ranging from 5 to 7.

(2) To the slurry prepared in the foregoing stage (1), there was added 1.5 L of a solution (30° C.) containing 1.2 mole/L of ammonium nitrate and 0.10 mole/L of silver nitrate to give a slurry liquid and the latter was then stirred for 16 hours.

(3) To the slurry liquid prepared in the foregoing stage (2), there was added 1.5 L of a 0.10 mole/L zinc nitrate solution (30° C.) to give a slurry liquid (a reaction solution) having an overall volume of 4.8 L. The pH value of the reaction solution was found to be 7.4.

(4) The reaction solution prepared in the stage (3) was stirred at 30° C. and a stirring rate of 150 rpm over 16 hours to thus subject the zeolite particles to an ion-exchange reaction under ion-exchangeable equilibrium conditions. During the ion-exchange reaction, zinc nitrate was dissolved in the reaction solution to thus increase the zinc nitrate concentration of the reaction solution.

(5) The zeolite phase was separated from the reaction solution obtained in the foregoing stage (4) through filtration and then excess silver ions and zinc ions were removed by washing the filtered zeolite phase with water maintained at a temperature ranging from 15 to 60° C.

(6) The zeolite phase obtained in the foregoing stage (5) was dried by heating the same at 110° C. to thus form antibacterial zeolite particles which were hereunder referred to as Sample No. 4.

Preparation of Sample No. 5:

(1) To 1 kg of Zeolite Y particles dried by heating at 110° C., there was added water to give 1.3 L of a slurry, the slurry was subsequently stirred for the degassing thereof, and a proper amount of a 0.5N nitric acid solution and water were further added to the slurry to thus give 1.8 L of a slurry whose pH value was adjusted to a level ranging from 5 to 7.

(2) To the slurry prepared in the foregoing stage (1), there was added 1.5 L of a solution (30° C.) containing 0.30 mole/L of silver nitrate to give a slurry liquid and the latter was then stirred for 16 hours.

(3) To the slurry liquid prepared in the foregoing stage (2), there was added 1.5 L of a 0.30 mole/L zinc nitrate solution (30° C.) to give a slurry liquid (a reaction solution) having an overall volume of 4.8 L. The pH value of the reaction solution was found to be 7.1.

(4) The reaction solution prepared in the stage (3) was stirred at 30° C. and a stirring rate of 150 rpm over 16 hours to thus subject the zeolite particles to an ion-exchange reaction under ion-exchangeable equilibrium conditions. During the ion-exchange reaction, zinc nitrate was dissolved in the reaction solution to thus increase the zinc nitrate concentration of the reaction solution.

(5) The zeolite phase was separated from the reaction solution obtained in the foregoing stage (4) through filtration and then excess silver ions and zinc ions were removed by washing the filtered zeolite phase with water maintained at a temperature ranging from 15 to 60° C.

(6) The zeolite phase obtained in the foregoing stage (5) was dried by heating the same at 110° C. to thus form antibacterial zeolite particles which were hereunder referred to as Sample No. 5.

Various data concerning the Sample Nos. 1 to 5 thus obtained are summarized in the following Table 1:

TABLE 1

| Sample No. | Yield (g) | Ion Concentrations (% by mass) in the Region Extending over the Depth Ranging from 0 to 1 nm from the Particle Surface | | | |
|---|---|---|---|---|---|
| | | $NH_4$ | Ag | Zn | Ag/Zn (X) |
| 1 | 940 | 1.2 | 0.3 | 10.2 | 0.029 |
| 2 | 940 | 0.8 | 1.9 | 11.0 | 0.173 |
| 3 | 940 | — | 3.0 | 15.5 | 0.194 |
| 4 | 950 | 0.4 | 2.4 | 5.9 | 0.407 |
| 5 | 940 | — | 8.6 | 14.6 | 0.589 |

| Sample No. | Ion Concentrations (% by mass) in the Region Extending over the Depth Ranging from 5 to 10 nm from the Particle Surface | | | | |
|---|---|---|---|---|---|
| | $NH_4$ | Ag | Zn | Ag/Zn (Y) | (X/Y)* |
| 1 | 1.4 | 0.5 | 7.5 | 0.066 | 0.439 |
| 2 | 1.0 | 2.6 | 7.7 | 0.338 | 0.512 |
| 3 | — | 5.5 | 12.0 | 0.458 | 0.424 |
| 4 | 0.6 | 3.7 | 3.6 | 1.028 | 0.396 |
| 5 | — | 12.0 | 11.9 | 1.008 | 0.584 |

*This means the ratio (X/Y) in which X represents the ratio of the silver ion concentration to the zinc ion concentration as determined for the region within the zeolite particles extending over the depth ranging from 0 to 1 nm from the surface of the zeolite particles and Y represents the ratio of the silver ion concentration to the zinc ion concentration as determined for the region within the zeolite particles extending over the depth ranging from 5 to 10 nm from the surface of the zeolite particles All of these Samples Nos. 1 to 5 each have an X/Y value of less than 1. This clearly indicates that the ratio (A/B) of the silver ion concentration (A) to the zinc ion concentration (B) increases in the direction along the depth of each zeolite particle.

Example 2

In this Example 2, three kinds of antibacterial zeolite particle samples (Sample Nos. 6 to 8) were prepared by carrying out the ion-exchange treatment of the starting zeolite particles first in the presence of silver ions and subsequently in the coexistence of silver and zinc ions.

Preparation of Sample No. 6:
(1) To 1 kg of Zeolite A particles dried by heating at 110° C., there was added water to give 1.3 L of a slurry, the latter was subsequently stirred to degas the same and then a proper amount of a 0.5N nitric acid solution and water were further added to the slurry to thus give 1.8 L of a slurry whose pH value was adjusted to a level ranging from 5 to 7.
(2) To the slurry prepared in the foregoing stage (1), there was added 1.5 L of a solution (80° C.) containing 1.5 mole/L of ammonium nitrate and 0.01 mole/L of silver nitrate to give a slurry liquid and the latter was then stirred for 10 hours to thus subject the zeolite particles to an ion-exchange reaction under ion-exchangeable equilibrium conditions
(3) To the slurry liquid prepared in the foregoing stage (2), there was added 1.5 L of a 2.0 mole/L zinc nitrate solution to give a slurry liquid having an overall volume of 4.8 L. The pH value of the slurry liquid was found to be 7.4.
(4) The slurry liquid prepared in the stage (3) was stirred at 50° C. and a stirring rate of 150 rpm over 6 hours to thus subject the zeolite particles to an ion-exchange reaction under ion-exchangeable equilibrium conditions.
(5) The zeolite phase was separated from the slurry liquid obtained in the foregoing stage (4) through filtration and then excess silver ions and zinc ions were removed by washing the filtered zeolite phase with water maintained at a temperature ranging from 15 to 60° C.
(6) The zeolite phase obtained in the foregoing stage (5) was dried by heating the same at 110° C. to thus form antibacterial zeolite particles which were hereunder referred to as Sample No. 6.

Preparation of Sample No. 7:
(1) To 1 kg of Zeolite X particles dried by heating at 110° C., there was added water to give 1.3 L of a slurry, the latter was subsequently stirred to degas the same and then a proper amount of a 0.5N nitric acid solution and water were further added to the slurry to thus give 1.8 L of a slurry whose pH value was adjusted to a level ranging from 5 to 7.
(2) To the slurry prepared in the foregoing stage (1), there was added 1.5 L of a solution (80° C.) containing 1.2 mole/L of ammonium nitrate and 0.10 mole/L of silver nitrate to give a slurry liquid and the latter was then stirred for 10 hours to thus subject the zeolite particles to an ion-exchange reaction under ion-exchangeable equilibrium conditions.
(3) To the slurry liquid prepared in the foregoing stage (2), there was added 1.5 L of a 1.0 mole/L zinc nitrate solution to give a slurry liquid having an overall volume of 4.8 L. The pH value of the slurry liquid was found to be 7.4.
(4) The slurry liquid prepared in the stage (3) was stirred at 50° C. and a stirring rate of 150 rpm over 6 hours to thus subject the zeolite particles to an ion-exchange reaction under ion-exchangeable equilibrium conditions.
(5) The zeolite phase was separated from the slurry liquid obtained in the foregoing stage (4) through filtration and then excess silver ions and zinc ions were removed by washing the filtered zeolite phase with water maintained at a temperature ranging from 15 to 60° C.
(6) The zeolite phase obtained in the foregoing stage (5) was dried by heating the same at 110° C. to thus form antibacterial zeolite particles which were hereunder referred to as Sample No. 7.

Preparation of Sample No. 8:
(1) To 1 kg of Zeolite Y particles dried by heating at 110° C., there was added water to give 1.3 L of a slurry, the latter was subsequently stirred to degas the same and then a proper amount of a 0.5N nitric acid solution and water were further added to the slurry to thus give 1.8 L of a slurry whose pH value was adjusted to a level ranging from 5 to 7.
(2) To the slurry prepared in the foregoing stage (1), there was added 1.5 L of a solution (80° C.) containing 0.30 mole/L of silver nitrate to give a slurry liquid and the latter was then stirred for 10 hours to thus subject the zeolite particles to an ion-exchange reaction under ion-exchangeable equilibrium conditions.
(3) To the slurry liquid prepared in the foregoing stage (2), there was added 1.5 L of a 3.0 mole/L zinc nitrate solution to give a slurry liquid having an overall volume of 4.8 L. The pH value of the slurry liquid was found to be 7.1.
(4) The slurry liquid prepared in the stage (3) was stirred at 50° C. and a stirring rate of 150 rpm over 6 hours to thus subject the zeolite particles to an ion-exchange reaction under ion-exchangeable equilibrium conditions.
(5) The zeolite phase was separated from the slurry liquid obtained in the foregoing stage (4) through filtration and then excess silver ions and zinc ions were removed by washing the filtered zeolite phase with water maintained at a temperature ranging from 15 to 60° C.

(6) The zeolite phase obtained in the foregoing stage (5) was dried by heating the same at 110° C. to thus form antibacterial zeolite particles which were hereunder referred to as Sample No. 8.

Various data concerning the Sample Nos. 6 to 8 thus obtained are summarized in the following Table 2:

TABLE 2

| Sample | Yield | Ion Concentrations (% by mass) in the Region Extending over the Depth Ranging from 0 to 1 nm from the Particle Surface | | | |
|---|---|---|---|---|---|
| No. | (g) | $NH_4$ | Ag | Zn | Ag/Zn (X) |
| 6 | 930 | 1.0 | 0.3 | 10.3 | 0.029 |
| 7 | 940 | 0.4 | 2.5 | 5.5 | 0.455 |
| 8 | 940 | — | 8.7 | 14.6 | 0.596 |

| Sample | Ion Concentrations (% by mass) in the Region Extending over the Depth Ranging from 5 to 10 nm from the Particle Surface | | | | |
|---|---|---|---|---|---|
| No. | $NH_4$ | Ag | Zn | Ag/Zn (Y) | (X/Y) |
| 6 | 1.6 | 0.5 | 7.9 | 0.063 | 0.460 |
| 7 | 0.7 | 3.5 | 3.9 | 0.897 | 0.507 |
| 8 | — | 12.0 | 12.0 | 1.000 | 0.596 |

All of these Samples Nos. 6 to 8 each have an X/Y value of less than 1. This clearly indicates that the ratio (A/B) of the silver ion concentration (A) to the zinc ion concentration (B) increases in the direction along the depth of each zeolite particle.

Example 3

In this Example 3, three kinds of antibacterial zeolite particle samples (Sample Nos. 9 to 11) were prepared by the following two stage ion-exchange reaction: the first ion-exchange reaction with a silver ion-containing reaction solution (first reaction solution); and the second ion-exchange reaction with a zinc ion-containing reaction solution (second reaction solution).

Preparation of Sample No. 9:

(1) To 1 kg of Zeolite A particles dried by heating at 110° C., there was added water to give 1.3 L of a slurry, the latter was subsequently stirred to degas the same and then a proper amount of a 0.5N nitric acid solution and water were further added to the slurry to thus give 1.8 L of a slurry whose pH value was adjusted to a level ranging from 5 to 7.

(2) To the slurry prepared in the foregoing stage (1), there was added 3.0 L of a solution (30° C.) containing 1.5 mole/L of ammonium nitrate and 0.01 mole/L of silver nitrate to give a slurry liquid having an overall volume of 4.8 L (a first reaction solution). The pH value of the first reaction solution was found to be 7.4.

(3) The first reaction solution was stirred at 30° C. and a stirring rate of 150 rpm over 16 hours to thus subject the zeolite particles to an ion-exchange reaction under ion-exchangeable equilibrium conditions.

(4) The zeolite phase was separated from the first reaction solution obtained in the foregoing stage (3) through filtration.

(5) To the zeolite phase recovered in the foregoing stage (4), there was added 3.0 L of a 2.0 mole/L zinc nitrate solution to give a slurry liquid (a second reaction solution). The pH value of the second reaction solution was found to be 7.4.

(6) The second reaction solution was stirred at 30° C. and a stirring rate of 150 rpm over 16 hours to thus subject the zeolite particles to an ion-exchange reaction under ion-exchangeable equilibrium conditions.

(7) The zeolite phase was separated from the second reaction solution through filtration and then excess silver ions and zinc ions were removed by washing the filtered zeolite phase with water maintained at a temperature ranging from 15 to 60° C.

(8) The zeolite phase obtained in the foregoing stage (7) was dried by heating the same at 110° C. to thus form antibacterial zeolite particles which were hereunder referred to as Sample No. 9.

Preparation of Sample No. 10:

(1) To 1 kg of Zeolite X particles dried by heating at 110° C., there was added water to give 1.3 L of a slurry, the latter was subsequently stirred to degas the same and then a proper amount of a 0.5N nitric acid solution and water were further added to the slurry to thus give 1.8 L of a slurry whose pH value was adjusted to a level ranging from 5 to 7.

(2) To the slurry prepared in the foregoing stage (1), there was added 3.0 L of a solution (30° C.) containing 1.2 mole/L of ammonium nitrate and 0.10 mole/L of silver nitrate to give a slurry liquid having an overall volume of 4.8 L (a first reaction solution). The pH value of the first reaction solution was found to be 6.8.

(3) The first reaction solution was stirred at 30° C. and a stirring rate of 150 rpm over 16 hours to thus subject the zeolite particles to an ion-exchange reaction under ion-exchangeable equilibrium conditions.

(4) The zeolite phase was separated from the first reaction solution obtained in the foregoing stage (3) through filtration.

(5) To the zeolite phase recovered in the foregoing stage (4), there was added 3.0 L of a 1.0 mole/L zinc nitrate solution to give a slurry liquid (a second reaction solution). The pH value of the second reaction solution was found to be 6.8.

(6) The second reaction solution was stirred at 30° C. and a stirring rate of 150 rpm over 16 hours to thus subject the zeolite particles to an ion-exchange reaction under ion-exchangeable equilibrium conditions.

(7) The zeolite phase was separated from the second reaction solution through filtration and then excess silver ions and zinc ions were removed by washing the filtered zeolite phase with water maintained at a temperature ranging from 15 to 60° C.

(8) The zeolite phase obtained in the foregoing stage (7) was dried by heating the same at 110° C. to thus form antibacterial zeolite particles which were hereunder referred to as Sample No. 10.

Preparation of Sample No. 11:

(1) To 1 kg of Zeolite Y particles dried by heating at 110° C., there was added water to give 1.3 L of a slurry, the latter was subsequently stirred to degas the same and then a proper amount of a 0.5N nitric acid solution and water were further added to the slurry to thus give 1.8 L of a slurry whose pH value was adjusted to a level ranging from 5 to 7.

(2) To the slurry prepared in the foregoing stage (1), there was added 3.0 L of a solution (30° C.) containing 0.30 mole/L of silver nitrate to give a slurry liquid having an overall volume of 4.8 L (a first reaction solution). The pH value of the first reaction solution was found to be 6.5.

(3) The first reaction solution was stirred at 30° C. and a stirring rate of 150 rpm over 16 hours to thus subject the zeolite particles to an ion-exchange reaction under ion-exchangeable equilibrium conditions.

(4) The zeolite phase was separated from the first reaction solution obtained in the foregoing stage (3) through filtration.

(5) To the zeolite phase recovered in the foregoing stage (4), there was added 3.0 L of a 3.0 mole/L zinc nitrate solution to give a slurry liquid (a second reaction solution). The pH value of the second reaction solution was found to be 6.5.

(6) The second reaction solution was stirred at 30° C. and a stirring rate of 150 rpm over 16 hours to thus subject the zeolite particles to an ion-exchange reaction under ion-exchangeable equilibrium conditions.

(7) The zeolite phase was separated from the second reaction solution through filtration and then excess silver ions and zinc ions were removed by washing the filtered zeolite phase with water maintained at a temperature ranging from 15 to 60° C.

(8) The zeolite phase obtained in the foregoing stage (7) was dried by heating the same at 110° C. to thus form antibacterial zeolite particles which were hereunder referred to as Sample No. 11.

Various data concerning the Sample Nos. 9 to 11 thus obtained are summarized in the following Table 3:

TABLE 3

| Sample | Yield | Ion Concentrations (% by mass) in the Region Extending over the Depth Ranging from 0 to 1 nm from the Particle Surface | | | |
|---|---|---|---|---|---|
| No. | (g) | NH$_4$ | Ag | Zn | Ag/Zn (X) |
| 9 | 940 | 1.1 | 0.3 | 10.7 | 0.028 |
| 10 | 940 | 0.5 | 2.6 | 5.4 | 0.481 |
| 11 | 950 | — | 8.7 | 14.6 | 0.596 |

| Sample | Ion Concentrations (% by mass) in the Region Extending over the Depth Ranging from 5 to 10 nm from the Particle Surface | | | | |
|---|---|---|---|---|---|
| No. | NH$_4$ | Ag | Zn | Ag/Zn (Y) | (X/Y) |
| 9 | 1.7 | 0.5 | 7.8 | 0.064 | 0.438 |
| 10 | 0.6 | 3.3 | 3.7 | 0.892 | 0.539 |
| 11 | — | 11.7 | 11.7 | 1.000 | 0.596 |

All of these Samples Nos. 9 to 11 each have an X/Y value of less than 1. This clearly indicates that the ratio (A/B) of the silver ion concentration (A) to the zinc ion concentration (B) increases in the direction along the depth of each zeolite particle.

Comparative Example

Preparation of Sample No. 0:

(1) To 1 kg of Zeolite A particles dried by heating at 110° C., there was added water to give 1.3 L of a slurry, the latter was subsequently stirred to degas the same and then a proper amount of a 0.5N nitric acid solution and water were further added to the slurry to thus give 1.8 L of a slurry whose pH value was adjusted to a level ranging from 5 to 7.

(2) To the slurry prepared in the foregoing stage (1), there was added 1.5 L of a solution (30° C.) containing 1.5 mole/L of ammonium nitrate and 0.01 mole/L of silver nitrate to give a slurry liquid and the latter was then stirred for 16 hours.

(3) To the slurry liquid prepared in the foregoing stage (2), there was added 1.5 L of a 2.0 mole/L zinc nitrate solution (30° C.) to give a slurry liquid (a reaction solution) having an overall volume of 4.8 L. The pH value of the reaction solution was found to be 7.3.

(4) The reaction solution prepared in the stage (3) was stirred at 30° C. and a stirring rate of 150 rpm over 16 hours to thus subject the zeolite particles to an ion-exchange reaction under ion-exchangeable equilibrium conditions.

(5) The zeolite phase was separated from the reaction solution obtained in the foregoing stage (4) through filtration and then excess silver ions and zinc ions were removed by washing the filtered zeolite phase with water maintained at a temperature ranging from 15 to 60° C.

(6) The zeolite phase obtained in the foregoing stage (5) was dried by heating the same at 110° C. to thus form antibacterial zeolite particles which were hereunder referred to as Sample No. 0.

Various data concerning the Sample No. 0 thus obtained are summarized in the following Table 4:

TABLE 4

| Sample | Yield | Ion Concentrations (% by mass) in the Region Extending over the Depth Ranging from 0 to 1 nm from the Particle Surface | | | |
|---|---|---|---|---|---|
| No. | (g) | NH$_4$ | Ag | Zn | Ag/Zn (X) |
| 0 | 940 | 1.2 | 0.5 | 9.5 | 0.053 |

| Sample | Ion Concentrations (% by mass) in the Region Extending over the Depth Ranging from 5 to 10 nm from the Particle Surface | | | | |
|---|---|---|---|---|---|
| No. | NH$_4$ | Ag | Zn | Ag/Zn (Y) | (X/Y) |
| 0 | 1.2 | 0.5 | 9.5 | 0.053 | 1.000 |

Sample No. 0 has the ratio (X/Y) equal to 1, in which X represents the ratio of the silver ion concentration to the zinc ion concentration as determined for the region within the zeolite particles extending over the depth ranging from 0 to 1 nm from the surface of the zeolite particles and Y represents the ratio of the silver ion concentration to the zinc ion concentration as determined for the region within the zeolite particles extending over the depth ranging from 5 to 10 nm from the surface of the zeolite particles. Accordingly, this Sample No. 0 corresponds to a comparative sample with respect to the present invention.

Test Example 1

The resistance to molds of the antibacterial zeolite particles obtained in Examples and Comparative Example were evaluated on the basis of the MIC value (ppm) against the following three kinds of molds.

The strains used herein are as follows: *Aspergillus niger* (NBRC6341); *Penicillium citrinum* (NBRC6352); and *Chaetomium globosum* (NBRC6347). The results thus obtained are summarized in the following Table 5.

TABLE 5

| | MIC (ppm) | | |
|---|---|---|---|
| Sample No. | *Aspergillus niger* | *Penicillium citrinum* | *Chaetomium globosum* |
| 1 | 500 | 500 | 500 |
| 2 | 500 | 500 | 500 |
| 3 | 500 | 500 | 500 |
| 4 | 500 | 500 | 500 |
| 5 | 250 | 250 | 250 |
| 6 | 500 | 500 | 500 |
| 7 | 500 | 500 | 500 |
| 8 | 250 | 250 | 250 |
| 9 | 500 | 500 | 500 |
| 10 | 500 | 500 | 500 |
| 11 | 250 | 250 | 250 |
| 0 | 500 | 500 | 500 |

The data listed in Table 5 clearly indicate that all of the antibacterial zeolite particles prepared in Examples (Sample Nos. 1 to 11) each possess an MIC value of less than or equal to 500 ppm. It would thus be appreciated, from this fact, that the antibacterial zeolite particles according to the present invention show excellent resistance to mold.

Test Example 2

The antibacterial zeolite particles obtained in Examples and Comparative Example were inspected for the antibacterial activities by the determination of the MIC (ppm) values against the following two kinds of bacteria:

The bacterial strains used herein were as follows: *Escherichia coli* (Number of Bacterial Strain-Preservation: NBRC3972) and *Staphylococcus aureus* (Number of Bacterial Strain-Preservation: NBRC12732).

The antibacterial zeolite particles obtained in Examples and Comparative Example were dried by heating (at 200° C. for 3 hours), each of the zeolite products was then incorporated into a variety of resins listed in the following Table 6 through kneading in an amount of 1% by mass and the resulting resin containing the zeolite was injection-molded (using Injection Molding Machine PLUS250 available from TOSHIBA MACHINE CO., LTD.) into each corresponding sample of resin-molded articles.

Each sample of the resin-molded articles thus formed was used in the test for examining antibacterial activity according to JIS Z2801. The following Table 6 shows the kinds of resins used for forming molded articles and the results obtained in the antibacterial activity test.

TABLE 6

| Sample No. | Kind of Resin Used | Antibacterial Activity Value | |
|---|---|---|---|
| | | *Escherichia coli* | *Staphylococcus aureus* |
| 1 | Polyethylene | 4.7 | 3.7 |
| 2 | Polypropylene | 4.0 | 3.5 |
| 3 | ABS | 4.1 | 3.7 |
| 4 | Polyamide | 3.9 | 3.8 |
| 5 | Polyethylene | 4.6 | 4.2 |
| 6 | Polyethylene | 3.7 | 3.4 |
| 7 | Polyamide | 4.0 | 3.5 |
| 8 | Polyethylene | 4.6 | 4.1 |
| 9 | Polyethylene | 3.7 | 3.6 |
| 10 | Polyamide | 3.7 | 3.6 |
| 11 | Polyethylene | 4.2 | 4.2 |
| 0 | Polyethylene | 3.0 | 2.9 |

Note:
Polyethylene: Petrocene 207R available from Tosoh Corporation
Polypropylene: J707WT available from Grand Polymer Co., Ltd.
ABS: Srylack 220 available from Asahi Kasei Corporation
Polyamide: Novamid 1010 available from Mitsubishi Engineering-Plastics Corporation
Polyethylene: NUC8009 available from Nippon Unicar Company Limited As will be clear from the data listed in Table 6, the whole resin molded articles prepared from the antibacterial zeolite particles of Examples (Sample Nos. 1 to 11) show antibacterial activity of more than or equal to 2.0 (a rate of extinction of higher than or equal to 99%). It would thus be appreciated, from this fact, that the resin composition containing the antibacterial zeolite particles according to the present invention possesses excellent antibacterial activity (antibacterial properties).

Test Example 3

Test for Examining Color Change

In this Test Example, a resin to which one of the antibacterial zeolite particle products of Examples and Comparative Example was compounded was exposed to strong ultraviolet light rays over a long period of time to thus inspect the resin for the discoloration-resistant properties.

The antibacterial zeolite particles obtained in Examples and Comparative Example were dried by heating (at 200° C. for 3 hours), each of the zeolite products was then incorporated into a variety of resins listed in the following Table 7 through kneading in an amount of 1% by mass and the resulting resin containing the zeolite was injection-molded (using Injection Molding Machine PLUS250 available from TOSHIBA MACHINE CO., LTD.) into each corresponding sample of resin-molded articles.

Each sample of the resulting resin-molded articles was irradiated with the ultraviolet light rays emitted from a black light (100 W; available from TOSHIBA LIGHTING & TECHNOLOGY CORPORATION), arranged at a point 15 cm apart from the sample, for 100 hours.

The color change observed was evaluated while using the color difference $\Delta E$ between respective color values in the L*-a*-b* calorimetric system observed before and after the light-irradiation treatment. In this respect, each color value was determined for each sample placed on white Kent paper using the MINOLTA colorimetric color difference meter CR-300.

The following Table 7 shows the kinds of resins used for forming molded articles and the results obtained in the color change test.

TABLE 7

| Sample No. | Kind of Resin Used | Color Difference $\Delta E$ |
|---|---|---|
| 1 | Polyethylene | 0.05 |
| 2 | Polypropylene | 0.05 |
| 3 | ABS | 0.04 |
| 4 | Polyamide | 0.02 |
| 5 | Polyethylene | 0.09 |
| 6 | Polyethylene | 0.06 |
| 7 | Polyamide | 0.06 |
| 8 | Polyethylene | 0.12 |
| 9 | Polyethylene | 0.05 |
| 10 | Polyamide | 0.04 |
| 11 | Polyethylene | 0.11 |
| 0 | Polyethylene | 7.02 |

The resin molded article prepared using Sample No. 0 of Comparative Example underwent a color change and therefore, had a large color difference $\Delta E$. On the other hand, all of the resin molded articles prepared using Sample Nos. 1 to 11 according to Examples did not undergo any color change and had very small color differences $\Delta E$. It would be appreciated, in the light of this fact, that the resin composition containing the antibacterial zeolite particles according to the present invention possesses excellent discoloration-resistant properties.

It would likewise be appreciated, in the light of the results obtained in the foregoing Test Examples 1 to 3, that the antibacterial zeolite particles and the resin composition containing the particles according to the present invention show excellent discoloration-resistant properties, while maintaining excellent antibacterial properties.

INDUSTRIAL APPLICABILITY

The antibacterial zeolite particles of the present invention can be used as a raw material for preparing antibacterial products.

What is claimed is:
1. A method for producing antibacterial zeolite particles whose ion-exchangeable ions have completely or partially been replaced with silver ions and zinc ions, wherein the ratio (A/B) of the silver ion concentration (A) to the zinc ion concentration (B) in the antibacterial zeolite particles increases in the direction along the depth of each zeolite particle, comprising the steps of:
- (i) providing zeolite particles;
- (ii) adding a solution of a silver salt and a zinc salt to the zeolite particles to initiate an ion-exchange reaction; and
- (iii) continuing the ion-exchange reaction while gradually adding the zinc salt to a mixture obtained in the step (ii).

2. A method for producing antibacterial zeolite particles whose ion-exchangeable ions have completely or partially been replaced with silver ions and zinc ions, wherein the ratio (A/B) of the silver ion concentration (A) to the zinc ion concentration (B) in the antibacterial zeolite particles increases in the direction along the depth of each zeolite particle, comprising the steps of:
- (i) providing zeolite particles;
- (ii) adding a solution of a silver salt to the zeolite particles to initiate an ion-exchange reaction, wherein, the solution is free of any zinc ion;
- (iii) adding a solution of a zinc salt to a mixture obtained in the step (ii); and
- (iv) continuing the ion-exchange reaction.

3. A method for producing antibacterial zeolite particles whose ion-exchangeable ions have completely or partially been replaced with silver ions and zinc ions, wherein they have a ratio: (X/Y) of less than 1, in which (X) represents the ratio of the silver ion concentration to the zinc ion concentration as determined for the region within the zeolite particles extending over the depth ranging from 0 to 1 nm from the surface of the zeolite particles and (Y) represents the ratio of the silver ion concentration to the zinc ion concentration as determined for the region within the zeolite particles extending over the depth ranging from 5 to 10 nm from the surface of the zeolite particles, comprising the steps of:
- (i) providing zeolite particles;
- (ii) adding a solution of a silver salt and a zinc salt to the zeolite particles to initiate an ion-exchange reaction; and
- (iii) continuing the ion-exchange reaction while gradually adding the zinc salt to a mixture obtained in the step (ii).

4. A method for producing antibacterial zeolite particles whose ion-exchangeable ions have completely or partially been replaced with silver ions and zinc ions, wherein they have a ratio: (X/Y) of less than 1, in which (X) represents the ratio of the silver ion concentration to the zinc ion concentration as determined for the region within the zeolite particles extending over the depth ranging from 0 to 1 nm from the surface of the zeolite particles and (Y) represents the ratio of the silver ion concentration to the zinc ion concentration as determined for the region within the zeolite particles extending over the depth ranging from 5 to 10 nm from the surface of the zeolite particles, comprising the steps of:
- (i) providing zeolite particles;
- (ii) adding a solution of a silver salt to the zeolite particles to initiate an ion-exchange reaction, wherein, the solution is free of any zinc ion;
- (iii) adding a solution of a zinc salt to a mixture obtained in the step (ii); and
- (iv) continuing the ion-exchange reaction.

* * * * *